United States Patent
Paul et al.

(10) Patent No.: US 10,080,591 B2
(45) Date of Patent: Sep. 25, 2018

(54) LATERAL SPINE STABILIZATION DEVICES AND METHODS

(75) Inventors: David C. Paul, Phoenixville, PA (US); Sean Suh, Bensalem, PA (US); Jody L. Seifert, Birdsboro, PA (US); Mark Fromhold, Ardmore, PA (US)

(73) Assignee: Globus Medical Inc, Audubon, PA (US)

( * ) Notice: Subject to any disclaimer, the term of this patent is extended or adjusted under 35 U.S.C. 154(b) by 197 days.

(21) Appl. No.: 13/029,175

(22) Filed: Feb. 17, 2011

(65) Prior Publication Data

US 2012/0215260 A1 Aug. 23, 2012

(51) Int. Cl.
*A61B 17/70* (2006.01)
*A61F 2/44* (2006.01)

(52) U.S. Cl.
CPC ........ *A61B 17/707* (2013.01); *A61B 17/7053* (2013.01); *A61B 17/7062* (2013.01); *A61F 2/4405* (2013.01)

(58) Field of Classification Search
CPC ........... A61B 17/7062–17/7071; A61F 2/4405
USPC ................................................. 606/246–279
See application file for complete search history.

(56) References Cited

U.S. PATENT DOCUMENTS

| | | | |
|---|---|---|---|
| 2003/0191471 A1* | 10/2003 | Michelson | 606/61 |
| 2004/0153071 A1* | 8/2004 | Zucherman et al. | 606/61 |
| 2006/0100705 A1* | 5/2006 | Puno | A61F 2/30771 623/17.11 |
| 2006/0241601 A1* | 10/2006 | Trautwein et al. | 606/61 |
| 2008/0114455 A1* | 5/2008 | Lange | A61B 17/7062 623/17.16 |
| 2008/0183211 A1* | 7/2008 | Lamborne | A61B 17/7068 606/249 |
| 2008/0228225 A1* | 9/2008 | Trautwein et al. | 606/246 |
| 2009/0234389 A1* | 9/2009 | Chuang et al. | 606/249 |
| 2010/0106190 A1* | 4/2010 | Linares | 606/249 |
| 2010/0137916 A1* | 6/2010 | Hynes | A61B 17/7059 606/280 |
| 2010/0204732 A1* | 8/2010 | Aschmann | A61B 17/7062 606/249 |
| 2011/0190819 A1* | 8/2011 | Trautwein | A61B 17/1606 606/249 |
| 2011/0218572 A1* | 9/2011 | Lechmann et al. | 606/249 |

FOREIGN PATENT DOCUMENTS

WO WO 2007098288 A2 * 8/2007

* cited by examiner

*Primary Examiner* — Nicholas Plionis

(57) ABSTRACT

A resilient core is positioned between bony projections which are offset from a principal load bearing region of a spinal joint. Shaped projections extend from the core, and engage the bony projections by conforming to anatomical landmarks, and may be fastened to the bony projections. During flexion of the joint, the core absorbs some of the force of compression, and limits an extent to which the joint may compress. If the shaped projections are connected to the bony projections, extension of the joint is inhibited by the projections and the core, limiting the extent to which the joint may be distracted. In this manner, healing is fostered, and a weakened or damaged joint is protected from excessive movement.

18 Claims, 6 Drawing Sheets

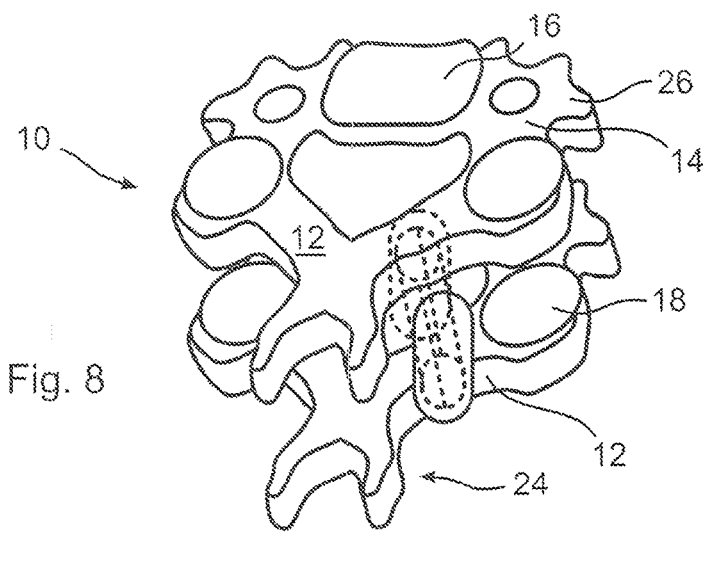
Fig. 8
Fig. 9A
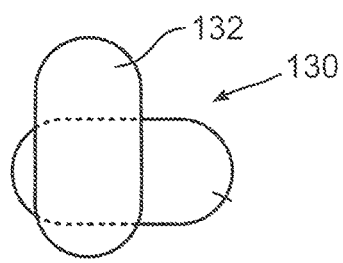
Fig. 9
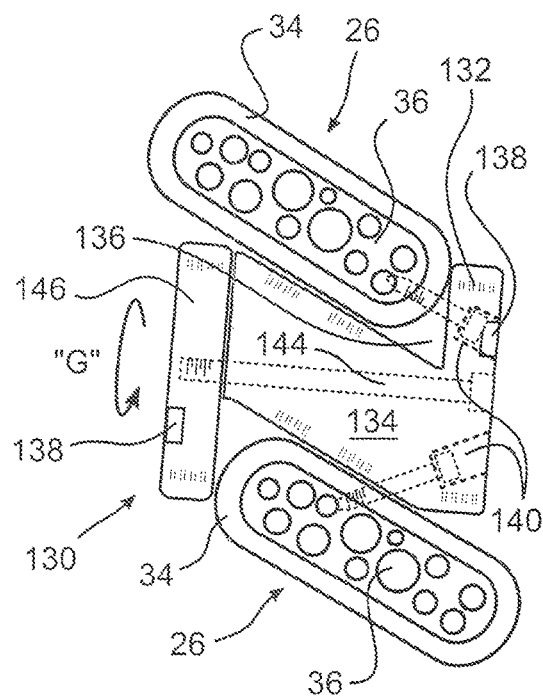

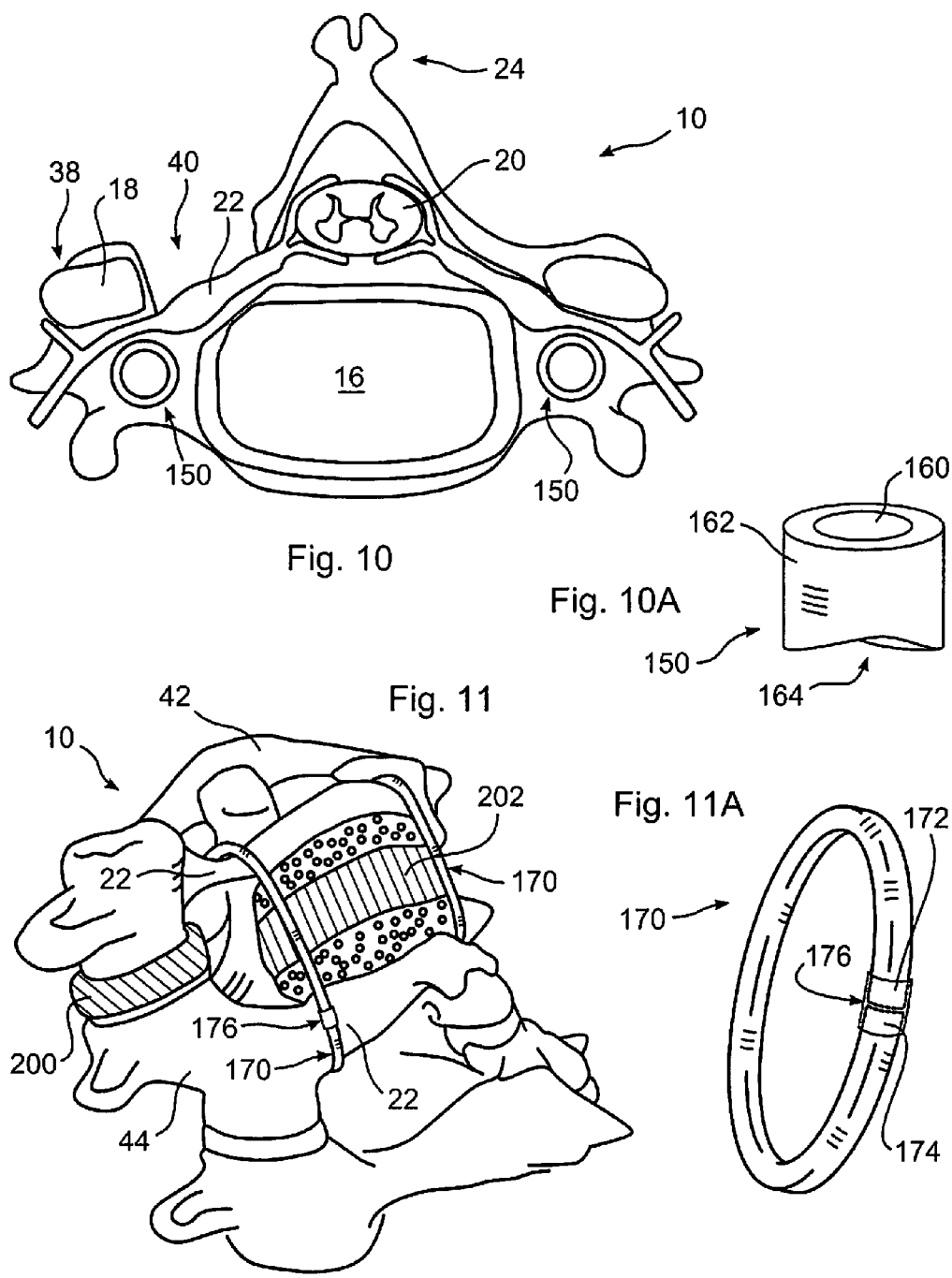

LATERAL SPINE STABILIZATION DEVICES AND METHODS

FIELD OF THE INVENTION

This invention relates to stabilizing adjacent vertebrae of the spine, after surgery or trauma, between bone portions at a distance from the vertebral body.

BACKGROUND OF THE INVENTION

Compression of a portion of the spinal cord or nerve root may be caused by trauma to the spine, or by a spinal disorder, for example spinal stenosis, degenerative disc disease, a bulging or herniated intervertebral disc, bone spurs, spondylosis, or spinal osteoarthritis. Surgery may be conducted upon the affected area to relieve the compression, however the problem may reoccur prior to complete healing, or due to an ongoing disease process.

Compression of nerve tissue may take place, for example, during bending, and in particular during lateral bending, where the disc annulus is damaged or weakened. During bending, the flexion side of the disc compresses and the extension side stretches. When the pressure of compression exceeds the tissue strength of the annulus, the nucleus may be extruded through the extension side, where it commonly compresses nerve tissue. This tends to occur more towards the posterior end of the vertebral column.

As an alternative to an anterior approach to the disc or other areas of the spine, a posterior approach including a foraminotomy may be performed to access the spinal cord and impinging tissue, and to relieve compression. During a foraminotomy, bone from the posterior arch of the spine over the nerve, or lamina, and possibly part of the facet joint, is removed using special cutting instruments and/or a drill. The neuroforamen may be enlarged in some cases to decompress the affected nerve portion. Additionally, portions of the disc may be removed.

Whether an anterior or posterior approach is taken, spine stability may be compromised due to the removal of supporting tissue, leaving the spine vulnerable to further damage.

SUMMARY OF THE INVENTION

In accordance with the invention, a supporting structure, stanchion, or strut includes a longitudinal body which is advantageously resilient, and superior and inferior braces connected to and extending from the body. The strut is sized and dimensioned to be inserted into the body at a location between bony extensions of adjacent vertebrae. The braces each contact and engage bony extensions of different vertebrae, and are advantageously shaped to conform to or surround at least a portion of the bony extensions.

In one embodiment of the invention, a strut of the invention is positioned between transverse processes of adjacent vertebrae. It should be understood, however, in accordance with the invention, that the strut may be positioned between any bony structure of adjacent vertebrae, which extends at a distance from the body of the vertebra, including but not limited to the pedicles, laminae, and spinous process, as well.

The superior and inferior braces of the strut of the invention may be configured to engage a respective extending bone by any known means, and may have a loose fitting engagement on upper and lower bones. Alternatively, one or both of the braces may be fastened to its respective bone, for example by bone screws, adhesive, or a clamp or strap. In one embodiment, one or both braces may be configured as a post, possibly with threads, which is inserted into a bony extension.

A strut in accordance with the invention may have a reduced height after compression during flexion, and if unconnected to bony extensions at the braces, a strut may have an original height on an extended side of the joint. If the braces of the invention are connected to the bones, however, a height of the strut may be greater than a resting height thereof.

In alternative embodiment of the invention, a strut is formed by two longitudinal panels that are connected by a cross member. The cross member may advantageously connect the panels at an angle, thereby forming two gaps into each of which a portion of a bony extension may reside, after implantation. The cross member may alternatively connect to one or both panels perpendicularly. Further, the cross member may connect to the panels in a different location upon each panel.

Selection of an attachment angle and location is based upon a general or imaged anatomy of the intended site of implantation. More particularly, bony extensions of the spine are not necessarily linearly aligned; rather, a healthy spine follows a complex curve which places analogous bony extensions at an offset angle with respect to one another. Moreover, the size of bony extensions may differ greatly between adjacent vertebrae. Selection of a suitable offset cross member or panel position enables the practitioner to form a fit which best serves the therapeutic needs of the individual patient. To enable the practitioner to modify the device during a procedure, the panel may be provided with a plurality of mounting points.

One or more of the panels, or the cross member, may be formed from a resilient material, to provide a desired amount of compression, twisting, and rebound force. The size and stiffness of the panels and cross member may be selected based upon an individual patient's needs, determined from preoperative consultation, examination, and imaging, or during the procedure. Accordingly, provision of a plurality of sizes and materials, and or the provision of suitable instrumentation, may be achieved using a kit.

The strut or panels may be provided with one or more boreholes operative to admit a screw, pin, or other fastener, whereby the strut or panel may be fastened to bone.

A strut of the invention may additionally be configurable, whereby the strut may be implanted in a first configuration, and changed during or after implantation to a second configuration. A connecting fastener is associated with the strut body, and is operative to releasably or rotatably connect a configurable panel to the body, whereby the strut may be more easily manipulated into a position within the body.

A strut of the invention is advantageously positioned adjacent to a resected area, for example a resected lamina, which may have been weakened, and advantageously but not necessarily an additional strut may be positioned at an opposite portion of the joint, for example in a corresponding location on an opposite side of the joint. In accordance with one use of the invention, for example, a foramen that has been treated, as by enlargement, may be protected from further narrowing.

Struts of the invention may be implanted using open or minimally invasive surgical techniques, and may be used in the context of non-instrumented procedures, as well as in combination with other implants, as would be understood by one skilled in the art.

A strut body, panel, or brace of the invention may be regularly shaped, or may be provided with one or more shaped or contoured engaging surfaces which conform to, and thereby interlock or engage with, existing or created anatomical landmarks. In this manner, the stability of the strut is improved, and the potential for migration of the strut from an intended location is reduced.

A strut of the invention advantageously includes one or more layers operative to provide additional functionality. In one embodiment, a layer has a different modulus of elasticity as compared with the remainder of the body, enabling complex damping or rebound characteristics. Additionally or alternatively, a layer may include a therapeutic substance, such as one or more of bone growth, antimicrobial, healing, or drug agents.

In accordance with an embodiment of the invention, a strut limits distraction of the joint during extension, by exerting a limiting force at a location at a distance from the body of the joint. The strut may advantageously be sized and shaped to weakly resist compression or twisting. As such, the joint has a greater range of motion, where needed.

Struts of the invention are advantageously formed with a flexible material, so that a limit of distraction is arrived at gradually, in a seemingly natural manner, rather than presenting an abrupt limit to a range of motion.

In another embodiment, a strut is passed or looped around the laminae, pedicles, spinous processes, or transverse processes, of adjacent vertebrae. Where there is no natural gap, or it is desired to avoid resecting a gap, the strut may be formed from a flexible strand, with ends joined within the body.

Devices of the invention are advantageously used in a context of non-instrumented joint stabilization, particularly as they may provide for sufficient stabilization to enable effective and timely fusion.

In accordance with the foregoing, struts of the invention are advantageously positioned at a distance from the vertebral body, or other weight bearing portion of the vertebral joint, and thus work to provide a laterally positioned stabilization for damaged or weakened joints. By being positioned laterally, struts of the invention benefit from added leverage attributable to being a distance from a fulcrum of the joint. Leverage is further improved by exploiting existing anatomy, such as the transverse process, to produce leverage at a distance from a fulcrum of the joint. As such, a device of the invention may be smaller than a device that stabilizes from within the vertebral body, and is easier to implant, with less trauma to the patient. Additionally, devices of the invention are advantageously implanted from a posterior approach, which is safer for the patient, and simpler for the practitioner. Moreover, implantation at a distance from a fulcrum of the joint concomitantly increases a working distance from the spinal cord, improving safety to the patient.

In accordance with one embodiment of the invention, a device is provided for stabilization of a joint having a weight bearing fulcrum, and bony extensions on different vertebrae extending away from the fulcrum. The device comprises a resilient core positionable between the bony extensions, operative to absorb a compressive force imparted to the core by the bony extensions, the force arising from flexion of the joint; and a shaped extension connected to the core, operative to engage a shape of the bony extensions, thereby stabilizing a position of the core; whereby the core and the shaped extension cooperate to promote a therapeutic maximum amount of joint movement.

In embodiments of the invention, the core and the shaped extension fit completely between the bony extensions; there are two of the shaped extensions, one of which is operative to engage a posterior face of one bony extension, and the other of which is operative to engage an anterior face of the other bony extension; there are two of the shaped extensions, one of which is operative to engage a superior face of one bony extension, and the other of which is operative to engage an inferior face of the other bony extension; a shaped extension is connected to a bony extension; a shaped extension is changeable with respect to the core, whereby implantation of the device is facilitated; the shaped extension is integrally formed with the core, and completely surrounds the bony extension; the device is positionable between bony extensions selected from the group consisting of lamina, pedicle, transverse process, articular process, spinous process, lateral mass junction, and inter-posterior arch; the core or shaped extension is fabricated from a material selected from the group consisting of: polymer, PEEK, HMWPE, metal, titanium alloy, chrome alloy, bone substitute material, natural material, bone, bone graft material, lyophilized tissue, autograft tissue, allograft tissue, xenograft tissue; the core or the shaped extension is provided with layers each having a different modulus of elasticity; the core or shaped extension is provided with a layer providing a therapeutic benefit selected from the group consisting of: bone growth promoting, antimicrobial, healing, therapeutic drug; the core is connected to the bony extensions, whereby the device is operative to impart a resistive force to distraction of the joint; the device is operative to impart a resistive force to compression of the joint; the core is connected to the bony extensions, and whereby the device is operative to impart both a resistive force to distraction of the joint, and a resistive force to compression of the joint; the resistive force to compression is different than the resistive force to distraction; and a plurality of devices are implanted within a joint.

In another embodiment of the invention, a device is provided for limiting movement of a joint of the spine, the joint having a principal weight bearing region and bony projections on each vertebra of the joint, the bony projections positioned at a distance from the principal weight bearing region, the device comprising a resilient core positionable to fit completely between a superior portion of the bony projection of one vertebra of the joint, and an inferior portion of the bony projection of the other vertebra of the joint; and at least one shaped extension connected to the core, sized and shaped to engage an anatomical landmark of at least one of the bony projections, thereby operative to affix a position of the core with respect to the joint; whereby flexion of the joint moves one bony projection closer to the other bony projection, thereby compressing the core, whereby a resistive force to compression is imparted by the core to the joint.

In various embodiments, there are two of the shaped extensions, each of the shaped extensions connected to a different bony projection by means selected from the group consisting of: bone screw, screw, adhesive, clamp, strap, pin, suture, and knot; and extension of the joint moves one bony projection further away from the other bony projection, thereby extending the core in connection with the shaped extensions, whereby a resistive force to distraction is imparted by the core to the joint.

In yet another embodiment of the invention, a device is provided for limiting movement of a joint of the spine, the joint having a principal weight bearing region and bony projections on each vertebra of the joint, the bony projections positioned at a distance from the principal weight bearing region, the device comprising a resilient core positionable to fit completely between a superior portion of the bony projection of one vertebra of the joint, and an inferior portion of the bony projection of the other vertebra of the joint; and two shaped extensions connected to the core, each sized and shaped to engage an anatomical landmark upon a bony projection of a different vertebra, thereby operative to affix a position of the core with respect to the joint, at least one of the shaped extensions movably connected to the core and operative to change an orientation of the shaped extension with respect to the core, whereby implantation of the device is facilitated; whereby flexion of the joint moves one bony projection closer to the other bony projection, thereby compressing the core, whereby a resistive force to compression is imparted by the core to the joint. In one alternative, at least one movably connected extension is rotatably connected to the core.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 8 illustrates a stylized depiction of adjacent vertebra, showing a positioning of a strut in accordance with FIG. 6;

FIG. 9 illustrates a section of configurable strut in accordance with the invention, implanted within the body;

FIG. 9A depicts the strut of FIG. 9, configured for implantation;

FIG. 10 illustrates a resection of a vertebra, stabilized by an alternative strut in accordance with the invention;

FIG. 10A depicts further detail of the strut of FIG. 10;

FIG. 11 illustrates two of an alternative strut in accordance with the invention, implanted in connection with cervical vertebrae C1 and C2; and FIG. 11A depicts further detail of the strut of FIG. 11.

DETAILED DESCRIPTION OF THE INVENTION

In the description which follows, any reference to direction or orientation is intended primarily and solely for purposes of illustration and is not intended in any way as a limitation to the scope of the present invention. Also, the particular embodiments described herein are not to be considered as limiting of the present invention.

Figure 1:
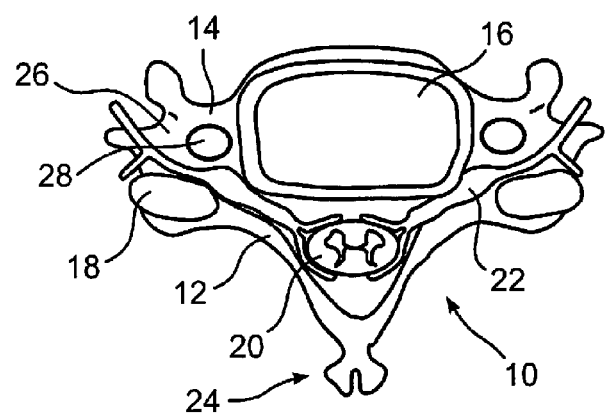
FIG. 1 depicts a cervical spine section of the human body.
Figure 1A:
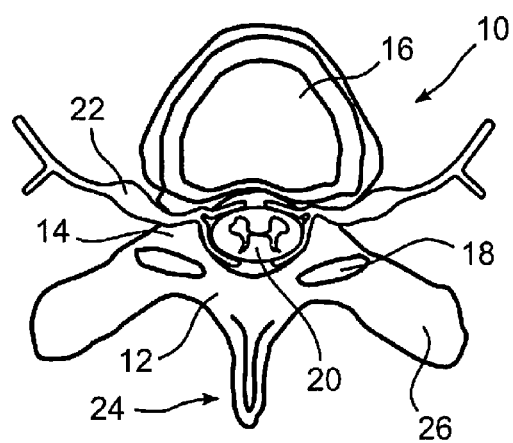
FIG. 1a depicts a thoracic spine section of the human body.
Figure 1B:
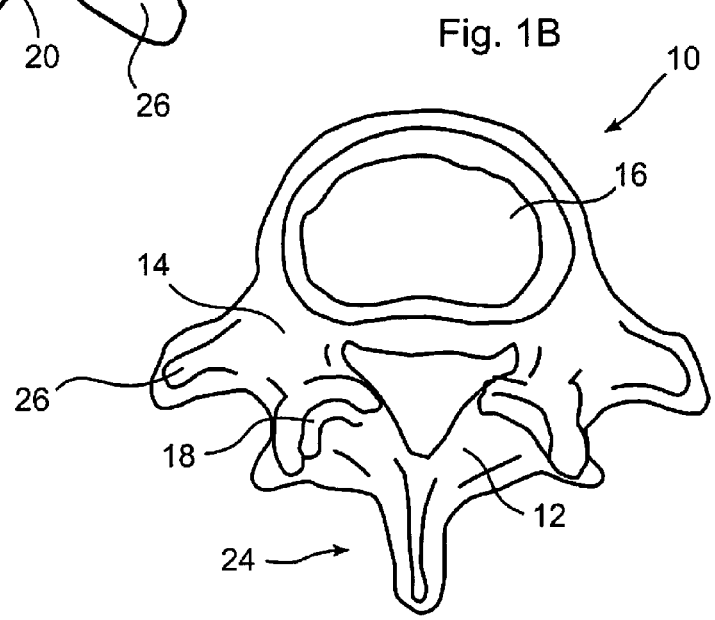
FIG. 1b depicts a lumbar spine section of the human body.

Referring now to the figures, in which like reference numerals refer to like elements, FIGS. 1 and 1B depict schematic illustrations of cervical, thoracic, and lumbar sections of a vertebral joint 10, respectively, of a spinal column, for reference purposes. The illustrations show the lamina 12, pedicle 14, body 16, superior articular process 18 of the facet joint, spinal cord 20, nerve root 22, spinous process 24, transverse process 26, and foramen 28. As used herein, reference 26 applies to the transverse process, or any other bony extension or projection, generally. It should be understood that the devices of the invention may be sized and shaped, as would be understood by one skilled in the art, to be used with any vertebral type.

Figure 2:
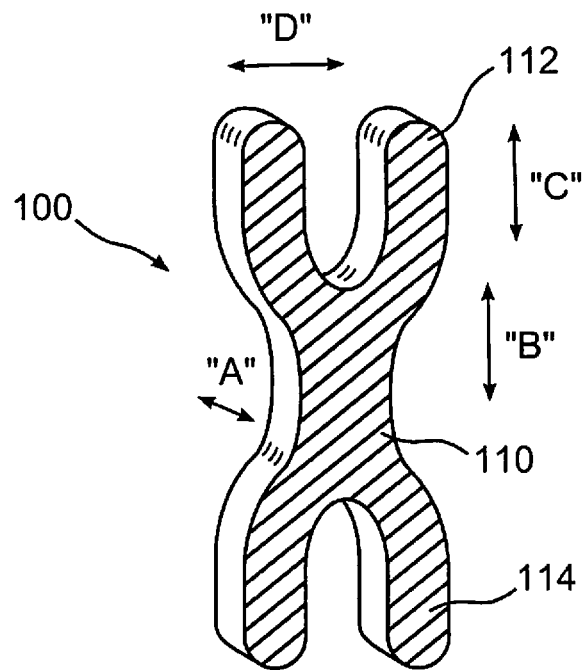
FIG. 2 depicts a strut in accordance with the invention.

With reference to FIG. 2, in accordance with the invention, a supporting structure, stanchion, or strut 100 includes a longitudinal body 110 which is advantageously resilient, and superior and inferior braces 112, 114, connected to and extending from body 110. Strut 100 is sized and dimensioned to be inserted into the body at a location between bony extensions or projections of adjacent vertebrae. Braces 112, 114 each contact and engage bony extensions of different vertebrae, and are advantageously shaped to conform and or surround at least a portion of the bony extensions, thereby to better retain a desired position in relation thereto.

Figure 3:
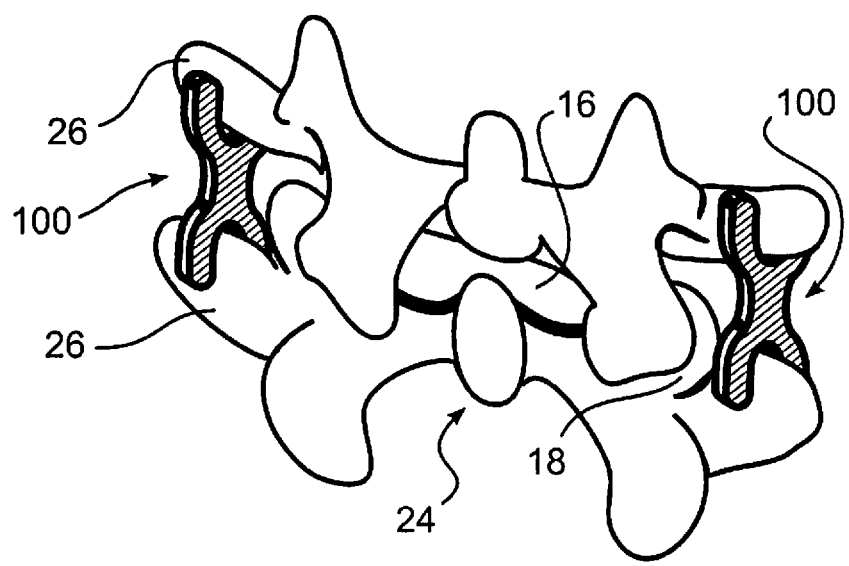
FIG. 3 illustrates a perspective view of two of the struts of FIG. 2, implanted in a stylized depiction of a vertebral joint.

In one embodiment of the invention, as shown in the diagrammatic perspective illustration of FIG. 3, strut 100 is positioned between transverse processes 26 of adjacent vertebrae. It should be understood, however, in accordance with the invention, strut 100 may be positioned between any bony structure of adjacent vertebrae, which extends at a distance from the body of the vertebra, including but not limited to the pedicles, laminae, and spinous process, as well. Moreover, strut 100 may be positioned between differing bony structures of adjacent vertebrae.

In the illustration of FIGS. 2 and 3, strut 100 is depicted as generally elongated; however a thickness "A" may be wider than what is shown, to increase stability and strength, according to the best therapeutic interests of the patient. Similarly, overall height "B" is selected for an optimal fit, as further described herein, wherein a height "B" may be selected to impart no biasing force, or alternatively a predetermined amount of biasing force, when the vertebral joint is neither flexed nor extended. Height "C" of superior or inferior brace 112, 114, and overall width "D", as well as the shape of brace 112, 114, is selected to best conform to the bone to which the respective brace 112, 114 is to be engaged, to improve stability and reduce the potential for migration. Braces 112, 114 may additionally be provided with shapes that engage landmarks which are introduced by the practitioner.

Superior and inferior brace 112, 114 may be configured, in accordance with the invention, to engage a respective extending bone by any known means, including, as illustrated in FIG. 3, a loose fitting engagement on upper and lower bones. Alternatively, one or both of braces 112, 114 may be fastened to its respective bone, for example by bone screws, adhesive, or a strap. In one embodiment, one or both of brace 112, 114 may be configured as a post, possibly with threads, which is inserted into a bony extension.

Figure 4:
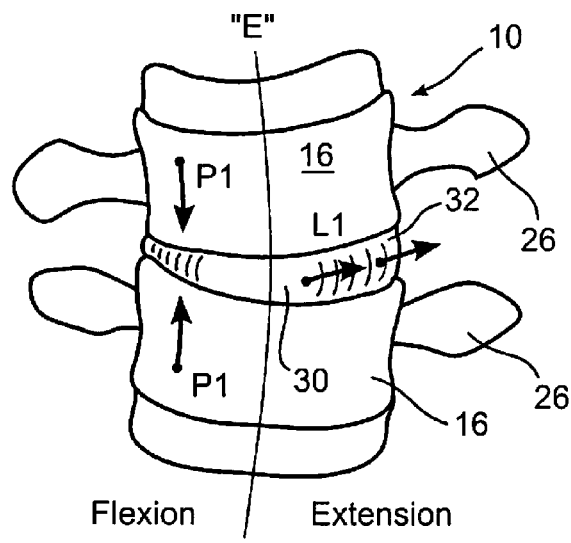
FIG. 4 shows forces acting upon a bending joint of the spine.

With reference now to FIG. 4, a stylized pair of adjacent vertebrae illustrates forces during joint movement, in vivo. Force arrows P1 illustrate compressive forces acting upon a side of the vertebral body when the side is flexed along the line indicated as "E". It can be seen that compressive force P1 acts upon disc 30 to shorten a portion 32 of disc 30 and thereby cause a lateral displacement of disc material indicated by arrows L1. When a disc is weakened by trauma or disease, this lateral displacement may become excessive, or the disc annulus may rupture, releasing a portion of the nucleus pulposus material, resulting in pressure upon a nerve root 22. Accordingly, use of strut 100 in accordance with the invention reduces the extent of bending, and or reduces the rate of bending, resulting in a reduced severity of disc deformation, and a reduction of pain. Additionally, use of strut 100 may be beneficial when it is desired to reduce or at least partially prevent bending, as during healing from treatment for disc herniation, for example. A strut in accordance with the invention may additionally be used in conjunction with known annulus repair devices.

Figure 5:
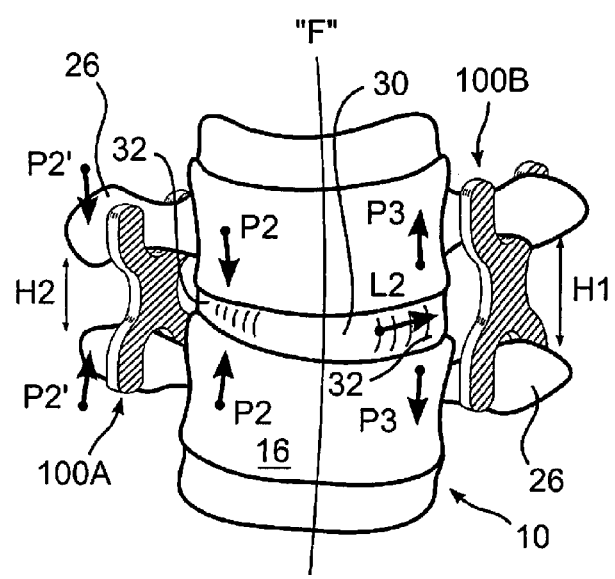
FIG. 5 shows the bending joint of FIG. 4, provided with two of the struts of FIG. 2, illustrating a change in acting forces.

Referring now to FIG. 5, struts 100A and 100B have been positioned between bony extensions 26 of two adjacent vertebrae. In FIG. 5, two struts 100A, 100B have been positioned between the adjacent vertebrae, although it should be understood that a therapeutic benefit may be obtained using only a single strut 100, advantageously but not necessarily positioned on a damaged side of a vertebra. In FIG. 5, during flexion, strut 100A is compressed by a shortening of a distance between bony projections 26 on a left side of the drawing. Thus, a force illustrated as P2' is applied to strut 100A, causing a reduction in compression force P2 as compared with force P1 of FIG. 4. Alternatively stated, force P2 is reduced due to the absorption of a portion of the total force imparted due to flexion, by strut 100A, resulting in a reduction or amelioration of the impact of flexion upon disc 30, and in particular, a reduction in a force of extrusion of disc portion 32. More particularly, the disc extrusion force at L2 of FIG. 5 is less than that of L1 of FIG. 4, due to the stabilization of strut 100A.

Strut 100A has a reduced height H2 after compression during flexion, and if unconnected to bony extensions 26 at braces 112, 114, an original height H1 on an extended side of the joint. If braces 112, 114 are connected, however, a height of strut 100B may be greater than a resting height thereof.

With further reference to FIGS. 4 and 5, on the extended side of the joint, a separating force P3 is exerted upon disc 30. If strut 100B is not fastened at bony extensions 26, extension will not be inhibited. However, should it be desired to limit extension, for example to foster the preservation of a degenerating disc, strut 100A and or 100B may be fastened to its respective bony extension. Accordingly, a stretching force (not shown) imparted to a strut 100 thus affixed, would produce a proportionate reduction in a force of extension imparted to disc 30.

Figure 6:
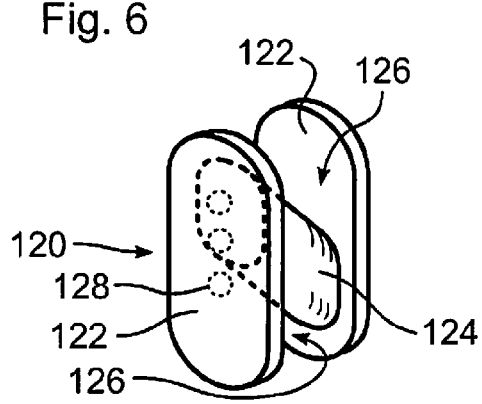
FIG. 6 depicts an alternative strut in accordance with the invention.
Figure 7:
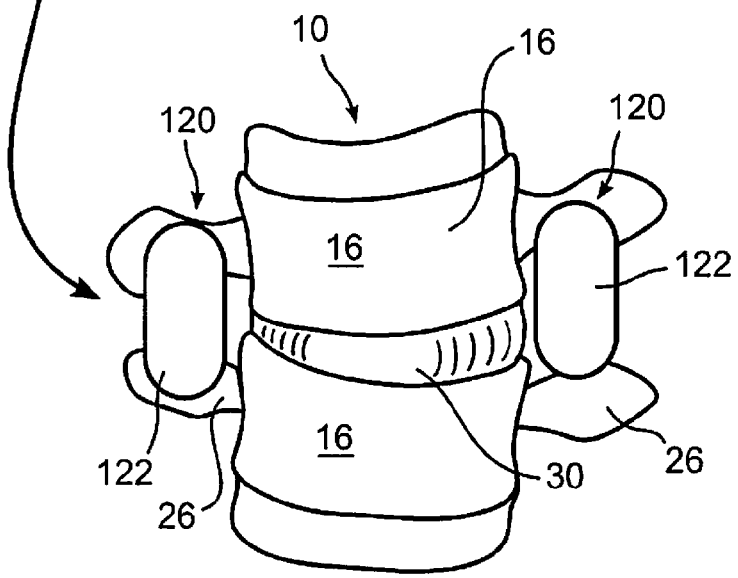
FIG. 7 illustrates two of the struts of FIG. 6, implanted between vertebrae.

In FIGS. 6 and 7, an alternative embodiment of the invention is illustrated as strut 120, which includes two longitudinal panels 122, connected by a cross member 124. In the illustrations, cross member 124 connects panels 122 at an angle, thereby forming two gaps 126 into each of which a portion of a bony extension may reside, after implantation, as illustrated in FIGS. 7-9. In the examples shown, panels 122 and cross member 124 form a shape akin to the letter "N". Cross member 124 may alternatively connect to one or both panels 122 perpendicularly. Further cross member 124 may connect to panels 122 in a different location upon each panel.

Selection of an attachment angle and location is based upon a general or imaged anatomy of the intended site of implantation. More particularly, bony extensions of the spine are not necessarily linearly aligned; rather, a healthy spine follows a complex curve which places analogous adjacent bone extensions at an offset angle with respect to one another. Moreover, the size of bony extensions may differ greatly between adjacent vertebrae. Selection of a suitable offset cross member 124 or panel 122 position enables the practitioner to form a fit which best serves the therapeutic needs of the individual patient. To enable the practitioner to modify the device during a procedure, panel 122 may be provided with a plurality of mounting points 128, through which a fastener may pass. Other adjustable means of attaching either or both panels 122 to cross member 124 may be provided, as would be understood by one skilled in the art.

One or more of panels 122, or cross member 124, may be formed from a resilient material, to provide a desired amount of compression, twisting, and rebound force. The size and stiffness of panels 122 and cross member 124 may be selected based upon an individual patient's needs, determined from preoperative consultation, examination, and imaging, or during a therapeutic procedure. Accordingly, provision of a plurality of sizes and materials, and or the provision of suitable instrumentation, may be achieved using a kit.

FIG. 8 illustrates a stylized pair of adjacent cervical vertebrae, in perspective, showing a position of strut 130 disposed between adjacent laminae. While cervical vertebrae are illustrated, it should be understood that strut 130 may be used with any adjacent vertebrae having adjacent bones between which an appropriately sized strut 130 may be positioned. Strut 100 may also be positioned as illustrated in FIG. 8, or either strut 100, 130 may alternatively or additionally be disposed between adjacent pedicles 14, or as detailed previously, between any adjacent bones extending from body 16. Alternatively, a combination of any of the struts in accordance with the invention may be used within a single patient.

FIG. 9 illustrates a stylized pair of adjacent bony extensions 26, comprising an outer cortical layer 34, and an inner cancellous layer 36. Strut 130 in accordance with the invention has been implanted between bony extensions 26, and is sized and shaped to conformingly engage bony extensions 26 within gaps 136 during at least a portion of the range of movement thereof. Strut 130 additionally illustrates grasping apertures 138 which may be formed within a surface of a strut in accordance with the invention, sized and shaped to engage an implantation or manipulation tool (not shown).

Strut 130 further illustrates one or more boreholes 140, advantageously countersunk, each operative to admit screw, pin or other fastener, whereby strut 130 may be fastened to bone, for example to bony extension 26. Such boreholes may additionally or alternatively be provided in one or more panels. All devices in accordance with the invention may be so adapted, to increase stability of the joint and/or the device, and to prevent migration of the device.

Strut 130 additionally illustrates a configurable fastener in accordance with the invention, whereby a strut of the invention may be implanted in a first configuration, and changed during or after implantation to a second configuration. A connecting fastener 144 associated with body 134 is provided, operative to releasably or rotatably connect a configurable panel 146 to body 134. In one embodiment, as illustrated in FIGS. 9 and 9A, panels 146 and 132 may be rotated relative to each other, as indicated by arrow "G", for example, whereby strut 130 may be more easily manipulated into a position within the body.

Referring now to FIG. 10, a schematic illustration of a spinal section includes a resected area 40 of lamina 12 and a portion of superior articular process 18 or another part of facet joint 38, and a portion of body 16. In this example, the resected area provides additional space for nerve root 22. It is desired to maintain this additional space over time, to prevent recurrence of adverse symptoms, due to, for example, further degeneration of adjacent bones. Accordingly, strut 150 of the invention is advantageously positioned adjacent to the resected area, which may have been weakened, and advantageously but not necessarily at an opposite portion of the joint, for example in a corresponding location on an opposite side of the joint. In accordance with one use of the invention, for example, a foramen that has been treated, as by enlargement, may be protected from further narrowing.

Struts of the invention may be implanted using open or minimally invasive surgical techniques, and may be used in the context of non-instrumented procedures, as well as in combination with other implants, as would be understood by one skilled in the art.

Strut 150, further illustrated in FIG. 10A, comprises a body 160 operative to be positioned upon a bony extension. Strut 150 thereby more readily fits between adjacent bony extensions where there is very limited space, for example between pedicles 14, as illustrated, or between lamina 12, or between transverse processes 26 which are vestigial. Strut body 160 may be regularly shaped, or as in the embodiment shown in FIG. 10A, may be provided with one or more shaped or contoured engaging surfaces 164 which conform to, and thereby interlock or engage with, existing or created anatomical landmarks. In this manner, the stability of strut 150 is improved, and the potential for migration of strut 150 from an intended location is reduced.

Strut 150 advantageously includes one or more layers 162 operative to provide additional functionality to strut 150. In one embodiment, layer 162 has a different modulus of elasticity as compared with body 160, enabling complex damping or rebound characteristics. Additionally or alternatively, layer 162 may include a therapeutic substance, such as one or more of bone growth, antimicrobial, healing, or drug agents. The layered structure shown and described for strut 150 may be applied to all struts of the invention.

With reference to FIG. 11, in accordance with the invention, strut 170 limits distraction of the joint during extension, by exerting a limiting force at a location at a distance from the body of the joint. Strut 170, in the embodiment of FIG. 11, is sized and shaped to weakly resist compression or twisting. As such, the joint between the C1 and C2 cervical vertebrae, or atlas 42 and axis 44, as illustrated, is particularly well suited to the use of strut 170, as a greater range of motion is typically desired therebetween. Strut 170 may also be used in other joint locations in the body, where it is desired to limit a distraction or separation of joint components, while providing lesser inhibition of other movements.

Strut 170 is advantageously formed with a flexible material, so that a limit of distraction is arrived at gradually, in a seemingly natural manner, rather than presenting as an abrupt limit to a range of motion.

Additionally, as with other struts of the invention, a single strut 170 may be used, to provide stabilization for a weakened portion of a joint. Alternatively, two, three, or more struts may be used, at a single joint level, or in multiple joints.

While the embodiment shown in FIG. 11 is thin and is intended to weakly resist compression, it should be understood that strut 170 may be sufficiently thick and or rigid to significantly resist compression or twisting, and may accordingly be fastened to upper and lower bone portions of the joint, using any known means, including clamps, screws, pin, adhesive, suturing, and knotting.

In FIG. 11, strut 170 is passed around laminae 22 of adjacent vertebrae 42, 44; however, strut 170 may alternatively be looped over adjacent pedicles, spinous processes, or transverse processes, for example. Where there is no natural gap, or it is desired to avoid resecting a gap, strut 170 may be formed from a flexible strand, with ends 172, 174 joined within the body. In one embodiment, a coupling 176 surrounds ends 172, 174, and is bonded in place, or ends 172, 174 are bonded to each other, by knotting, crimping, suturing, adhering, brazing, annealing, or any other method known in the art.

A strut 100, 130, 150, or 170 in accordance with the invention, may be combined with other stabilizing means. An example is illustrated in FIG. 11, in which flexible stabilization spacers 200, 202 have been positioned within the lateral mass junction and the inter-posterior arch of C1-C2 (42, 44), respectively. In accordance with the invention, a device of the invention is positioned at a junction located at a distance from the vertebral body; however atlas 42 uniquely has no body. Accordingly, in the example of FIG. 11, strut 170 is positioned at a junction located at a distance from a major or principal weight bearing portion of the joint. In this manner, strut 170 fulfills the role of preventing hyperextension of the unstable joint, and as described above, possibly resistance to compression as well, while the stabilization spacers are further operative to maintain a correct range of joint spacing at rest, and during movement.

Devices of the invention are advantageously used in a context of non-instrumented joint stabilization, particularly as they may provide for sufficient stabilization to enable effective and timely fusion.

Strut 170 may be fabricated from, or fabricated using, wire, cord, or cable, as a single or multiple strand, whose strands may be joined by any known means, including adhesion, coating, or weaving. Strut 170 may additionally be coated with one or more therapeutic layers, which may include bone growth, antimicrobial, or healing agents, or therapeutic drugs. Strut 170 may additionally be formed with layers of differing stiffness, as described for strut 150.

In accordance with the foregoing, struts of the invention are advantageously positioned at a distance from the vertebral body 16, or other such principal weight bearing portion of the vertebral joint, and thus work to provide a laterally positioned stabilization for damaged or weakened joints. By being positioned laterally, struts of the invention benefit from added leverage attributable to being a distance from a fulcrum of the joint. Leverage is further improved by exploiting existing anatomy, such as the transverse process, to produce leverage at a distance from a fulcrum of the joint. As such, a device of the invention may be smaller than a device that stabilizes from within the vertebral body, and is easier to implant, with less trauma to the patient. Additionally, devices of the invention are advantageously implanted from a posterior approach, which is safer for the patient, and simpler for the practitioner. Moreover, implantation at a distance from a fulcrum of the joint concomitantly increases a working distance from the spinal cord, improving safety to the patient.

Devices of the invention, including struts 100, 130, 150 and 170, may be fabricated using any biocompatible material having the requisite strength, durability, and flexibility, including polymers, such as PEEK or HMWPE, metals, such as titanium or chrome alloys, bone substitute material, and natural materials, such as bone or bone graft material, including lyophilized tissue, and autograft, allograft, or xenograft tissue. Additionally, devices in accordance with the invention may be fabricated from a material that biodegrades in the body during a therapeutically advantageous time interval.

Devices of the invention, including struts 100, 130, 150, and 170, are advantageously provided with smooth and or rounded surfaces, which reduce a potential for deleterious mechanical effects on neighboring tissues.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A device for stabilization of a joint, the device comprising:
    a strut having a first portion a second portion, the first portion and the second portion capable of being rotated with respect to each other, wherein the first portion comprises a panel and a body extending along a longitudinal axis, the body having an upper surface angled relative to the longitudinal axis and a lower surface angled relative to the longitudinal axis, wherein the angled upper surface and the angled lower surface are parallel to one another, wherein the panel has a height greater than the body, wherein the panel is fixed in position relative to the body, and wherein the panel is configured to attach to adjacent bony extensions;
    a connecting fastener extending along the longitudinal axis for connecting the first portion to the second portion, wherein the first portion or the second portion is rotated about the longitudinal axis;
    wherein the strut is positionable between the adjacent bony extensions comprising a superior bony extension and an inferior bony extension,
    wherein the panel comprises a first borehole and a second borehole, wherein the first borehole is angled in an upward direction and the second borehole is angled in a downward direction,
    wherein the first borehole is configured to receive a first fastener to secure the first portion to the superior bony extension and the second borehole is configured to receive a second fastener to secure the first portion to the inferior bony extension,
    wherein the first portion and the second portion each include at least one grasping structure for engagement with a tool,
    wherein the first borehole and the second borehole are countersunk into the first portion.

2. The device of claim 1, wherein the first portion is operative to engage a posterior face of the superior bony extension, and the second portion is operative to engage an anterior face of the inferior bony extension.

3. The device of claim 1, wherein the first portion is operative to engage a superior face of one bony extension, and the second portion is operative to engage an inferior face of the other bony extension.

4. The device of claim 1, wherein said device is positionable between bony extensions selected from the group consisting of lamina, pedicle, transverse process, articular process, lateral mass junction, and inter-posterior arch.

5. The device of claim 1, wherein said strut is fabricated from a material selected from the group consisting of: polymer, PEEK, HMWPE, metal, titanium alloy, chrome alloy, bone substitute material, natural material, bone, bone graft material, lyophilized tissue, autograft tissue, allograft tissue, xenograft tissue.

6. The device of claim 1, wherein said strut is provided with layers each having a different modulus of elasticity.

7. The device of claim 1, wherein said strut is provided with a layer providing a therapeutic benefit selected from the group consisting of: bone growth promoting, antimicrobial, healing, therapeutic drug.

8. The device of claim 1, wherein said strut is operative to impart a resistive force to distraction of the joint.

9. The device of claim 1, wherein said strut is operative to impart a resistive force to compression of the joint.

10. The device of claim 1, wherein said strut is operative to impart both a resistive force to distraction of the joint, and a resistive force to compression of the joint.

11. The device of claim 10, wherein said resistive force to compression is different than said resistive force to distraction.

12. A device for stabilization of a joint, the device comprising:
    a strut having a first portion a second portion, wherein the first portion comprises a panel and a body extending along a longitudinal axis, the body having an upper surface angled relative to the longitudinal axis and a lower surface angled relative to the longitudinal axis, wherein the angled upper surface and the angled lower surface are parallel to one another, wherein the panel and the body form an angle relative to one another, wherein the panel is fixed in position relative to the body, and wherein the panel is configured to attach to adjacent bony extensions;
    a connecting fastener for connecting the first portion to the second portion;
    wherein the strut is positionable between the adjacent bony extensions comprising a superior bony extension and an inferior bony extension,
    wherein the first portion comprises a first borehole and a second borehole,
    wherein the first borehole is configured to receive a first fastener to secure the first portion to the superior bony extension and the second borehole is configured to receive a second fastener to secure the first portion to the inferior bony extension, wherein the first borehole is angled in an upward direction and the second borehole is angled in a downward direction,
    wherein the first borehole and the second borehole are countersunk into the first portion.

13. The device of claim 12, wherein the first portion is operative to engage a posterior face of the superior bony extension, and the second portion is operative to engage an anterior face of the inferior bony extension.

14. The device of claim 12, wherein the first portion is operative to engage a superior face of one bony extension, and the second portion is operative to engage an inferior face of the other bony extension.

15. The device of claim 12, wherein said strut is operative to impart both a resistive force to distraction of the joint, and a resistive force to compression of the joint.

16. The device of claim 12, wherein said strut is provided with layers each having a different modulus of elasticity.

17. The device of claim 12, wherein said strut is operative to impart a resistive force to compression of the joint.

18. The device of claim 17, wherein said resistive force to compression is different than a resistive force to distraction.

\* \* \* \* \*